United States Patent [19]

Verbeek et al.

[11] 4,295,990

[45] Oct. 20, 1981

[54] REAGENT FOR THE QUANTITATIVE DETERMINATION OF WATER

[75] Inventors: Antonie E. Verbeek; Jozef M. J. Mattheij, both of Deventer, Netherlands

[73] Assignee: J. T. Baker Chemicals B.V., Deventer, Netherlands

[21] Appl. No.: 157,440

[22] Filed: Jun. 9, 1980

[30] Foreign Application Priority Data

Jul. 26, 1979 [EP]  European Pat. Off. ........ 79102673.5

[51] Int. Cl.$^3$ ........................ G01N 31/00; C09K 3/00
[52] U.S. Cl. .................................. 252/408; 23/230 R
[58] Field of Search ......... 23/230 R, 230 HC, 230 M; 422/68, 75; 252/408

[56]  References Cited

U.S. PATENT DOCUMENTS 2,967,155  1/1961  Blomgren et al. .................. 252/408

FOREIGN PATENT DOCUMENTS 45-3637  6/1970  Japan ................................ 23/230 M

OTHER PUBLICATIONS

Verhoef, J. C. et al., Analytica Chimica Acta., vol. 94, (1977), pp. 395–403.
Schwartz, G. A. et al., Talanta, vol. 22, pp. 773–775, Pergammon Press, 1975.

*Primary Examiner*—William F. Smith
*Assistant Examiner*—Chris Konkol
*Attorney, Agent, or Firm*—George W. Rauchfuss, Jr.

[57]  ABSTRACT

A reagent for the quantitative determination of water in combination with a titration solution containing iodine is described. The reagent contains sulfur dioxide and an anhydrous alkali metal acetate in 2-methoxy ethanol or a mixture of 2-methoxy ethanol and methanol in a volume ratio of at least 10:90. The reagent is characterized in that when it is left to stand no precipitate forms and the increase in control value is kept to a minimum.

6 Claims, No Drawings

REAGENT FOR THE QUANTITATIVE DETERMINATION OF WATER

FIELD OF THE INVENTION

This invention relates to a reagent and method for quantitative determination of water in combination with a titration solution containing iodine.

BACKGROUND OF THE INVENTION

The usual method of quantitatively determining water is the Karl Fischer method, in which the substance under investigation is reacted with a solution of sulfur dioxide and iodine in a mixture of pyridine and methanol; see K. Fischer, Angew, Chemie, Vol. 48 (1935), p. 394. With water the reagent is converted into pyridine sulfate and hydrogen iodide with accompanying loss of color. The amount of iodine consumed is a measure of the water content of the substance. The reaction follows the equation:

$$SO_2 + I_2 + 2H_2O \rightarrow H_2SO_4 + 2HI$$

Determination by titration is a very precise method. With the aid of the reagent it is even possible to detect a water content of less than 0.01%; see Kirk and Othmer, Encyclopedia of Chemical Technology, 2nd edition, Vol. 2 (1963), pp. 673–677.

The Karl Fischer method has the drawback that the reaction is very slow, which means that titration is laborious and tedious and the end-point drags. The odor of sulfur dioxide and pyridine is disagreeable, so that it is even necessary to work under a hood. Another disadvantage is that the sulfur dioxide and iodine form the yellow $SO_2I^-$ complex, which makes it impossible to detect a visual end-point.

The limited shelf life, the instability of the titre, and the need for storage in a cool, dark place are further disadvantages.

Limited applicability and the inconsistency of the titration medium are further indicative of the problems faced by the analyst, despite the considerable improvements brought by the Karl Fischer method.

In a known development of this Karl Fischer method the problems of titrimetric determination of water are avoided; see J. C. Verhoef and E. Barendrecht, Analytica Chimica Acta, Vol. 94 (1977), pp. 395–403. This improved method makes use of two reagents, namely a solution of sodium acetate and sulfur dioxide in methanol (solution A) and a solution of iodine in methanol (titration solution B). In solution A, for example, the molarity for sodium acetate is 0.5 and the molarity for sulfur dioxide also 0.5. The solution has an APHA color index of 10 and the control value amounts to 0 to 4 ml of titration solution B for 20 ml of solution A. Titration solution B has a constant titre of 3.5 mg of $H_2O/ml$. Approximately 1 part titration solution B is required per 2 parts solution A.

The titration procedure is as follows: 20 ml of solution A is pre-titrated with titration solution B under continual stirring and in a moisture-free atmosphere. A specified amount of the hydrous substance under investigation is then quickly introduced into the titration vessel. The amount of the substance to be investigated (sample) should be in correct proportion to the estimated amount of water present. Taking into account the buffering capacity it is possible to determine 50 to 60 mg of water in 20 ml of solution A. The titration vessel is sealed, the burette adjusted and titration begun. The solution should be thoroughly mixed with a magnetic stirrer throughout the whole titration procedure.

The bipotentiometric method is used in the most conventional titration procedures to determine the end-point. Here reduction time is normally fixed at the point of equivalence at 20 seconds. The occurrence of yellow discoloration before the end-point is an indication for insufficient buffering capacity. This can be corrected by decreasing the sample amount or increasing the quantity of solution A. Using this method it is possible to smoothly carry out determination of water in alcohol, alkanes, aromatic hydrocarbons, aldehydes, ketones, ethers, esters, salts with water of crystallization, basic substances such as trishydroxymethylamino methane, lyophilized products, foodstuffs, molecular sieves and granular fertilizers. Visual end-point detection is also possible with this method.

This method has the disadvantage that when solution A is allowed to stand a milky-white murkiness or precipitate immediately forms, which is particularly adverse for the visual end-point detection. Moreover, the control value of solution A increases to an undesirably high degree as the solution ages and at rather high temperatures.

The problem underlying the invention is thus to develop a reagent for the quantitative determination of water consisting of solution A described above, used in combination with titration solution B, whereby the reagent does not form precipitates when left to stand and where the increase in control value is kept to a minimum.

SUMMARY OF THE INVENTION

The solution to this problem is based on the surprising finding that when, instead of methanol, 2-methoxy ethanol or a mixture of 2-methoxy ethanol and methanol is used as solvent for reagent solution A, and by reducing the amount of sulfur dioxide in solution A, the formation of a precipitate and the undesirably high increase in the control value can be avoided.

DETAILED DESCRIPTION OF THE INVENTION

The invention thus relates to a reagent for the quantitative determination of water in combination with a titration solution containing iodine. The reagent contains sulfur dioxide and an anhydrous alkali metal acetate in an anhydrous lower aliphatic alcohol as solvent, and is characterized in that the lower aliphatic alcohol is 2-methoxy ethanol or a mixture of 2-methoxy ethanol and methanol in a volume ration of at least 10:90. This reagent (solution A) is used in the known manner for the quantitative determination of water in combination with the titration solution B described above.

As the alkali metal acetate, solution A of the invention preferably contains anhydrous sodium acetate or anhydrous lithium acetate. For commercial reasons sodium acetate is preferred. The alkali metal acetate acts as a buffer; it is used in an amount of from 1.5 to 0.5 molar, preferably 1.2 to 0.8 molar, and especially 1.1 to 0.9 molar.

The sulfur dioxide is used in an amount of from 0.7 to 0.1 molar, preferably 0.5 to 0.2 molar, and especially 0.30 to 0.25 molar.

For titration solution B the iodine is used in an amount of from 0.3 to 0.1 molar, preferably 0.25 to 0.15 molar, and especially 0.23 to 0.19 molar.

It goes without saying that the reagent solutions contain these ingredients in suitable proportions to each other.

The solvent used for solution A and titration solution B, i.e. 2-methoxy ethanol, methanol or a mixture of 2-methoxy ethanol and methanol, should be as anhydrous as possible. Anhydrous is here understood to mean products with a water content of at most 0.05% by weight. Such products are commercially available.

Where a mixture of 2-methoxy ethanol and methanol is used for solution A, the preferred volume ration is 15:85 to 25:75.

The reagents for the quantitative determination of water are prepared as follows:

(a) Under stirring nitrogen is fed for 15 to 30 minutes into anhydrous 2-methoxy ethanol or into a mixture of anhydrous 2-methoxy ethanol and anhydrous methanol. This serves to eliminate any small amounts of air or oxygen from the solvent.

(b) The desired amount of anhydrous alkali metal acetate (dried at 120° to 150° C. for 15 to 30 hours) is then added under stirring in small portions and dissolved. At the same time nitrogen is bubbled into the solution.

(c) After the alkali metal acetate has completely dissolved nitrogen is bubbled into the solution under stirring for a further 15 to 30 minutes.

(d) Finally the desired amount of sulfur dioxide is introduced into the solution. The result is solution A.

Titration solution B is prepared as follows: The desired amount of iodine is introduced under stirring into anhydrous 2-methoxy ethanol, anhydrous methanol or a mixture of anhydrous 2-methoxy ethanol and anhydrous methanol and dissolved.

In tightly-sealed bottles solution A of the invention keeps well at a maximum of 15° C. and solution B at room temperature.

The following examples are illustrative of the invention.

EXAMPLE 1

Nitrogen is bubbled for 15 minutes with stirring into a mixture of 120.1 kg of anhydrous methanol and 36.5 kg of anhydrous 2-methoxy ethanol. 15.6 kg of anhydrous sodium acetate which has been dried for 24 hours at 150° C. is then introduced under stirring in small portions and dissolved. After the sodium acetate has completely dissolved nitrogen is bubbled with stirring for a further 15 minutes into the resulting solution. 6.1 kg of sulfur dioxide is then slowly introduced over a period of 4 hours. The result is solution A, which can be used in combination with a titration solution of iodine in methanol, 2-methoxy ethanol or a mixture of 2-methoxy ethanol and methanol for the quantitative determination of water.

Titration solution B is prepared by dissolving 5.4 kg of iodine in 79 kg of anhydrous methanol or 96 kg of anhydrous 2-methoxy ethanol.

EXAMPLE 2

Solution A is prepared in accordance with Example 1; however, instead of the mixture of 2-methoxy ethanol and methanol, 182.4 kg of anhydrous 2-methoxy ethanol, 15.6 kg of anhydrous sodium acetate and 6.1 kg of sulfur dioxide are used.

EXAMPLE 3

Example 1 is repeated, this time using a mixture of methanol and 2-methoxy ethanol in a volume ratio of 75:25 or alternatively 90:10.

These reagent solutions A also can be used in combination with titration solution B for the quantitative determination of water.

EXAMPLE 4

Examples 1 to 3 are repeated, this time using 12.5 kg of anhydrous lithium acetate instead of 15.6 kg of sodium acetate.

These solutions also can be successfully used in the manner described above for the quantitative determination of water.

EXAMPLE 5

Example 1 is repeated, this time using 3.33 kg of sulfur dioxide instead of 6.1 kg of sulfur dioxide.

The following table shows the stability of the control value (titration solution B consumed per 20 ml of solution A) of the solutions A prepared in accordance with Examples 1 and 5.

|  | Example 1 | Example 5 |
|---|---|---|
| at 5° C. | | |
| after 2 weeks | 0.9 ml | 1.2 ml |
| after 3 weeks | 0.9 ml | 1.2 ml |
| at 20° C. | | |
| start | 0.9 ml | 1.2 ml |
| after 2 weeks | 1.8 ml | 1.4 ml |
| after 3 weeks | 2.2 ml | 1.6 ml |
| at 40° C. | | |
| after 2 weeks | 4.3 ml | 2.2 ml |
| after 3 weeks | 6.1 ml | 2.7 ml |

From the table it is evident that the control value remains more stable when the solution contains less sulfur dioxide.

The following tests describe the use of the reagent solutions of the invention for the quantitative determination of water.

Test A

Water in petroleum ether, boiling range 100°–140° C., is determined with the aid of the reagent solution of Example 1 and the titration solution. The test is performed as follows:

20 ml of solution A is pre-titrated with titration solution B while stirring and agitating the reaction vessel and in a moisture-free atmosphere. 25 ml of petroleum ether is then quickly introduced into the titration vessel. Titration begins once the titration vessel has been sealed and the burette adjusted. 0.18 ml of titration solution B is consumed. This corresponds to a water content in the petroleum ether of 0.004 percent.

Test B

Test A is repeated using the reagent solution of Example 4. The petroleum ether has a water content of 0.004 percent.

In a further test the reagent solution of Example 4 is used to determine water in technical acetone. 5 ml of acetone is introduced into the titration vessel and consumes 2.28 ml of titration solution B. This corresponds to a water content in the acetone of 0.26 percent.

Test C

Test A is repeated using the reagent solution of Examples 1 and 5. The results are as follows:

| | |
|---|---|
| Water content of the petroleum ether using the reagent solution of Example 1 | = 0.004 percent |
| Water content of the petroleum ether using the reagent solution of Example 5 | = 0.004 percent |

In a further test with the reagent solution of Example 5 the water content of edible oil is determined. The test is performed as follows:

20 ml of solution A is pre-titrated with titration solution B while stirring and agitating the reaction vessel and in a moisture-free atmosphere. 10 ml of edible oil is then quickly introduced into the titration vessel. Titration begins once the titration vessel has been sealed and the burette adjusted. 1.13 ml of titration solution B is consumed. This corresponds to a water content in the edible oil of 0.05 percent.

We claim:

1. A reagent for the quantitative determination of water in combination with a titration solution containing iodine, which reagent contains sulfur dioxide and an anhydrous alkali metal acetate in an anhydrous lower aliphatic alcohol as solvent, characterized in that the lower aliphatic alcohol is selected from the group consisting of 2-methoxy ethanol or a mixture of 2-methoxy ethanol and methanol in a volume ratio of at least 10:90.

2. The reagent according to claim 1 wherein the alkali metal acetate is anhydrous lithium acetate.

3. The reagent according to claim 1 wherein the alkali metal acetate is anhydrous sodium acetate.

4. The reagent according to claim 1 characterized in that the mixture of 2-methoxy ethanol and methanol is in a volume ratio of 15:85 to 25:75.

5. The reagent according to claim 2 characterized in that the mixture of 2-methoxy ethanol and methanol is in a volume ratio of 15:85 to 25:75.

6. The reagent according to claim 3 characterized in that the mixture of 2-methoxy ethanol and methanol is in a volume ratio of 15:85 to 25:75.

* * * * *